US008532772B2

(12) United States Patent
Gunderson et al.

(10) Patent No.: US 8,532,772 B2
(45) Date of Patent: Sep. 10, 2013

(54) METHOD AND APPARATUS FOR POST-PROCESSING OF EPISODES DETECTED BY A MEDICAL DEVICE

(75) Inventors: Bruce D. Gunderson, Plymouth, MN (US); Mark L. Brown, North Oaks, MN (US); Amisha Somabhai Patel, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1081 days.

(21) Appl. No.: 11/564,135

(22) Filed: Nov. 28, 2006

(65) Prior Publication Data

US 2007/0123941 A1 May 31, 2007

Related U.S. Application Data

(60) Provisional application No. 60/740,219, filed on Nov. 28, 2005.

(51) Int. Cl.
*A61N 1/37* (2006.01)
(52) U.S. Cl.
USPC .................................. 607/27; 607/9; 607/28
(58) Field of Classification Search
USPC ....................... 600/509–510; 607/4–5, 27–28
See application file for complete search history.

(56) References Cited

U.S. PATENT DOCUMENTS

| 5,193,550 | A | 3/1993 | Duffin |
| 5,379,776 | A * | 1/1995 | Murphy et al. ............... 600/518 |
| 5,509,927 | A | 4/1996 | Epstein et al. |
| 5,527,344 | A | 6/1996 | Arzbaecher et al. |
| 5,545,186 | A | 8/1996 | Olson et al. |
| 5,755,739 | A | 5/1998 | Sun et al. |
| 5,776,168 | A | 7/1998 | Gunderson |
| 6,129,745 | A | 10/2000 | Sun et al. |
| 6,393,316 | B1 * | 5/2002 | Gillberg et al. ............... 600/515 |
| 6,470,210 | B1 | 10/2002 | Chen et al. |
| 6,669,631 | B2 | 12/2003 | Norris et al. |
| 6,748,269 | B2 | 6/2004 | Thompson et al. |
| 6,974,413 | B2 | 12/2005 | Bardy |
| 6,980,860 | B2 | 12/2005 | Stadler et al. |
| 7,047,083 | B2 | 5/2006 | Gunderson et al. |
| 7,103,404 | B2 | 9/2006 | Stadler et al. |
| 7,167,747 | B2 | 1/2007 | Gunderson et al. |
| 7,206,633 | B2 | 4/2007 | Saba |
| 7,212,849 | B2 | 5/2007 | Zhang et al. |
| 7,236,828 | B2 | 6/2007 | Casavant et al. |
| 7,280,869 | B2 | 10/2007 | Warman et al. |

(Continued)

OTHER PUBLICATIONS

Office Action from Chinese patent application No. 200680050423.8, dated Feb. 5, 2010, and translation thereof, 9 pp.

(Continued)

*Primary Examiner* — Rex R Holmes
(74) *Attorney, Agent, or Firm* — Michael C. Soldner

(57) ABSTRACT

A method and system of post-processing of sensing data generated by a medical device that includes transmitting a plurality of stored sensing data generated by the medical device to an access device, the stored sensing data including sensed atrial events and sensed ventricular events. The access device determines, in response to the transmitted data, instances where the medical device identified a cardiac event being detected in response to the sensing data, and determines, in response to the transmitted sensing data, whether one of the sensed ventricular events and the sensed atrial events is initiating conduction of a heart associated with the stored sensing data.

8 Claims, 9 Drawing Sheets

(56) References Cited

U.S. PATENT DOCUMENTS

| | | | |
|---|---|---|---|
| 7,289,851 | B2 | 10/2007 | Gunderson et al. |
| 7,333,855 | B2 | 2/2008 | Gunderson et al. |
| 7,369,893 | B2 | 5/2008 | Gunderson |
| 7,430,446 | B2 | 9/2008 | Li |
| 7,480,529 | B2 | 1/2009 | Li |
| 7,539,540 | B2 | 5/2009 | Gunderson et al. |
| 7,567,835 | B2 | 7/2009 | Gunderson et al. |
| 7,582,061 | B2 | 9/2009 | Li et al. |
| 7,738,950 | B2 | 6/2010 | Johnson et al. |
| 2003/0050563 | A1 | 3/2003 | Suribhotla et al. |
| 2003/0060849 | A1* | 3/2003 | Hsu ................................. 607/4 |
| 2003/0204146 | A1* | 10/2003 | Carlson ........................ 600/515 |
| 2003/0204215 | A1* | 10/2003 | Gunderson et al. ............. 607/27 |
| 2004/0015197 | A1* | 1/2004 | Gunderson ..................... 607/27 |
| 2005/0022181 | A1 | 1/2005 | Fox et al. |
| 2005/0080347 | A1 | 4/2005 | Sheth et al. |
| 2005/0192506 | A1 | 9/2005 | Kim et al. |
| 2006/0074331 | A1 | 4/2006 | Kim et al. |
| 2006/0217621 | A1 | 9/2006 | Kim et al. |
| 2006/0217769 | A1 | 9/2006 | Saba |
| 2006/0281998 | A1 | 12/2006 | Li |
| 2007/0123788 | A1 | 5/2007 | Gunderson et al. |
| 2007/0123789 | A1 | 5/2007 | Gunderson et al. |
| 2007/0123790 | A1 | 5/2007 | Gunderson et al. |
| 2007/0135863 | A1 | 6/2007 | Gunderson et al. |
| 2007/0135864 | A1 | 6/2007 | Gunderson et al. |
| 2007/0167986 | A1 | 7/2007 | Gunderson et al. |
| 2011/0112417 | A1 | 5/2011 | Gunderson et al. |

OTHER PUBLICATIONS

Office Action from U.S. Appl. No. 11/564,132 dated Jun. 18, 2010 (7 pages).

Response to Office Action from U.S. Appl. No. 11/564,132, filed Aug. 17, 2010 (7 pages).

Office Action from U.S. Appl. No. 11/564,126 dated Jun. 21, 2010 (7 pages).

Response to Office Action from U.S. Appl. No. 11/564,126, filed Aug. 20, 2010 (11 pages).

Office Action from U.S. Appl. No. 11/564,156 dated May 28, 2010 (7 pages).

Response to Office Action from U.S. Appl. No. 11/564,156, filed Jul. 28, 2010 (9 pages).

Office Action from U.S. Appl. No. 11/564,147 dated Jun. 18, 2010 (7 pages).

Response to Office Action from U.S. Appl. No. 11/564,147, filed Aug. 17, 2010 (12 pages).

Office Action from U.S. Appl. No. 11/564,139 dated Jul. 9, 2010 (9 pages).

International Search Report from corresponding PCT Application Serial No. PCT/US2006/045527, dated May 18, 2007 (2 pages).

Written Opinion from corresponding PCT Application Serial No. PCT/US2006/045527, dated May 18, 2007 (6 pages).

International Preliminary Report on Patentability from corresponding PCT Application Serial No. PCT/US2006/045527, dated Jun. 3, 2008 (7 pages).

Office Action from U.S. Appl. No. 11/564,120 dated May 22, 2009 (18 pages).

Amendment from U.S. Appl. No. 11/564,120 dated Aug. 24, 2009 (21 pages).

Office Action from U.S. Appl. No. 11/564,120 dated Sep. 25, 2009 (19 pages).

Amendment from U.S. Appl. No. 11/564,120 dated Nov. 25, 2009 (10 pages).

Advisory Action from U.S. Appl. No. 11/564,120 dated Dec. 9, 2009 (3 pages).

Office Action from U.S. Appl. No. 11/564,120 dated Jan. 28, 2010 (17 pages).

Amendment from U.S. Appl. No. 11/564,120 dated May 28, 2010 (10 pages).

Office Action from U.S. Appl. No. 11/564,120 dated Aug. 11, 2010 (13 pages).

Office Action from U.S. Appl. No. 11/564,147 dated Jun. 23, 2009 (9 pages).

Amendment from U.S. Appl. No. 11/564,147 dated Sep. 14, 2009 (12 pages).

Advisory Action from U.S. Appl. No. 11/564,147 dated Aug. 30, 2010 (3 pages).

European Office Action from corresponding European Application No. 06 844 584.0-1526 dated Sep. 2, 2010 (5 pages).

Request for Continued Examination from U.S. Appl. No. 11/564,147 dated Oct. 18, 2010 (1 page).

Amendment from U.S. Appl. No. 11/564,147 dated Oct. 18, 2010 (7 pages).

U.S. Appl. No. 12/906,821, filed Oct. 18, 2010 entitled "Method and Apparatus for Post-Processing of Episodes Detected by a Medical Device," by Gunderson et al.

Office Action from U.S. Appl. No. 12/906,821 dated Sep. 30, 2011 (8 pages).

Amendment filed in response to Office Action dated Sep. 30, 2011 from related U.S. Appl. No. 12/906,821, filed Jan. 30, 2012 (11 pages).

Office Action from U.S. Appl. No. 12/906,821 dated Apr. 5, 2012 (9 pages).

* cited by examiner

METHOD AND APPARATUS FOR POST-PROCESSING OF EPISODES DETECTED BY A MEDICAL DEVICE

CROSS REFERENCE TO RELATED APPLICATION

This is a utility application of and claims priority to provisional application U.S. Ser. No. 60/740,219 filed Nov. 28, 2005, entitled METHOD AND APPARATUS FOR POST-PROCESSING OF EPISODES DETECTED BY A MEDICAL DEVICE, incorporated herein by reference in its entirety.

CROSS-REFERENCE TO RELATED APPLICATIONS

Cross-reference is hereby made to the commonly assigned related U.S. Applications, Ser. No. 11/564,120, entitled "METHOD AND APPARATUS FOR POST-PROCESSING OF EPISODES DETECTED BY A MEDICAL DEVICE", to Gunderson et al.; Ser. No. 11/564,126, entitled "METHOD AND APPARATUS FOR POST-PROCESSING OF EPISODES DETECTED BY A MEDICAL DEVICE", to Gunderson et al.; Ser. No. 11/564,132, entitled "METHOD AND APPARATUS FOR POST-PROCESSING OF EPISODES DETECTED BY A MEDICAL DEVICE", to Gunderson et al.; Ser. No. 11/564,139, entitled "METHOD AND APPARATUS FOR POST-PROCESSING OF EPISODES DETECTED BY A MEDICAL DEVICE", to Gunderson et al.; Ser. No. 11/564,147, entitled "METHOD AND APPARATUS FOR POST-PROCESSING OF EPISODES DETECTED BY A MEDICAL DEVICE", to Gunderson et al.; Ser. No. 11/564,156, entitled "METHOD AND APPARATUS FOR POST-PROCESSING OF EPISODES DETECTED BY A MEDICAL DEVICE", to Gunderson et al.; all filed concurrently herewith and incorporated herein by reference in their entirety.

FIELD OF THE INVENTION

The present invention relates generally to medical devices, and more particularly to a method and apparatus for improved post-processing evaluation of episodes detected by a medical device.

BACKGROUND OF THE INVENTION

As memory and diagnostic capacity in implantable medical devices, such as implantable cardioverter-defibrillators (ICDs), for example, increase, the amount of time required to adequately review the available data associated to determine whether the detection of episodes and delivery of therapy by the device was appropriate also increases. Since the number of identified ICD indications continues to increase, while the amount of time that is available for post-process review of data decreases, the classification of ICD episodes requires significant levels of expertise. As a result, the number of clinicians having the required expertise has been reduced, which could result in a reduction in the quality of management of those patients having implanted devices. Therefore, an algorithm that post-processes and automatically reviews each previously detected episode upon interrogation could address these concerns by accurately classifying episodes and potentially suggesting ICD parameter changes and/or medical therapy, such as changes in medication, therapy delivery, use of ablation procedures, etc.

Reviewing the data stored in the ICD memory at clinic follow-up requires expert knowledge to discriminate between true ventricular arrhythmias and unnecessary detection of non-ventricular arrhythmias. As the ICD population increases, the time needed to review all ICD detected episodes with careful detail also increases. Automatically identifying ICD stored events that may have been inappropriately detected as episodes by the device may decrease the time required to review episodes and to assure that unnecessary detections are properly reviewed.

Therefore, an algorithm that correctly classifies each detected episode during post-processing review of data stored in an implantable device is needed in order to reduce the clinician time to review episodes, and to give the clinician confidence that each incorrect ICD detection was brought to their attention.

BRIEF DESCRIPTION OF THE DRAWINGS

Aspects and features of the present invention will be appreciated as the same becomes better understood by reference to the following detailed description of the embodiments of the invention when considered in connection with the accompanying drawings, wherein.

DETAILED DESCRIPTION OF THE INVENTION

Figure 1:
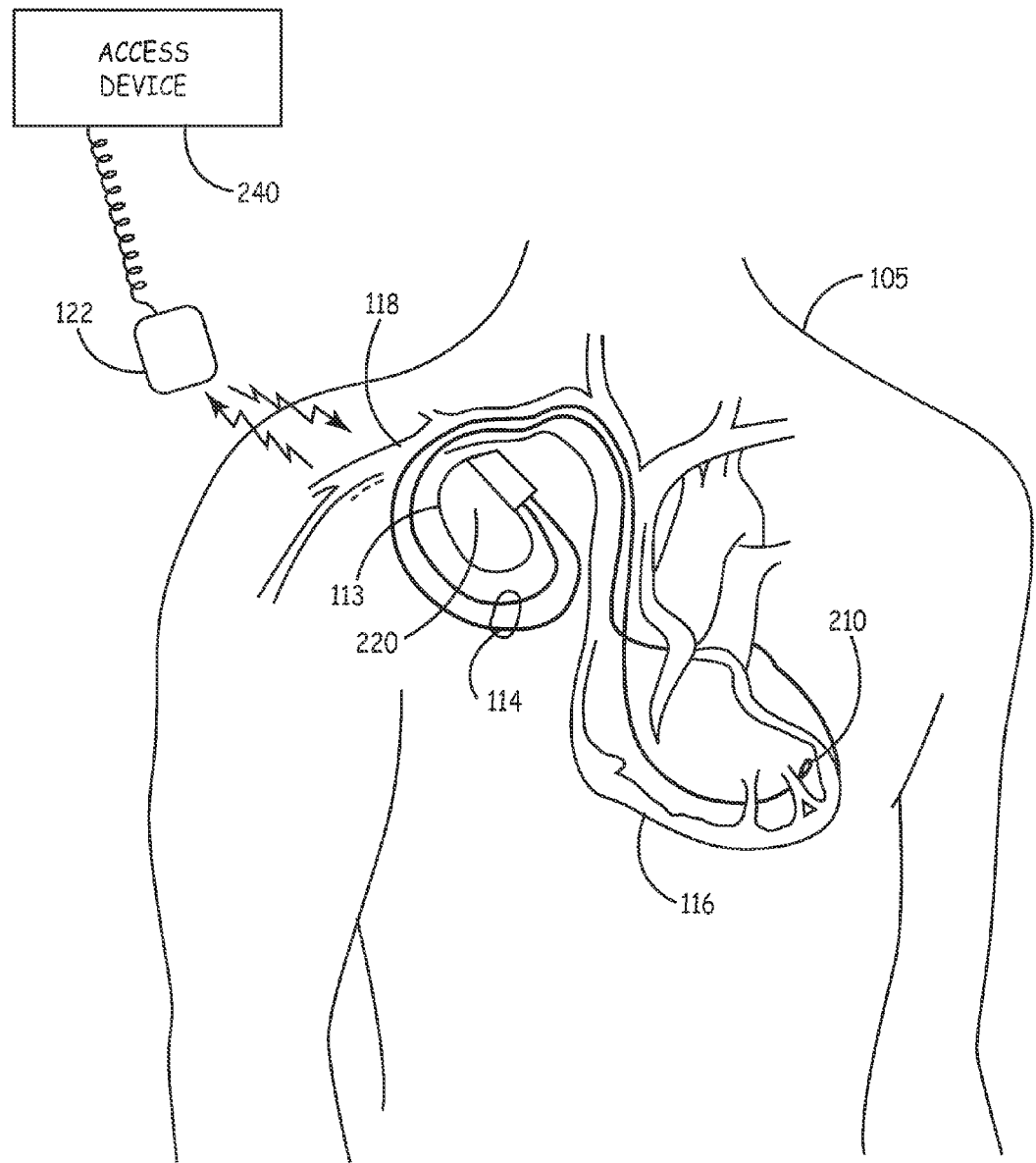
FIG. 1 is a schematic diagram of an exemplary implantable medical device system for classifying a cardiac event according to an embodiment of the present invention.

FIG. 1 is a schematic diagram of an exemplary implantable medical device system for classifying a cardiac event according to an embodiment of the present invention. As illustrated in FIG. 1, a system for classifying events according to an embodiment of the present invention includes an implantable medical device 220, such as implantable cardiac pacemaker, implantable cardioverter/defibrillator (ICD), or pacemaker/cardioverter/defibrillator, for example, electrically and mechanically attached to one or more leads 114 placed within the heart of the human body 105 that is used to acquire and process physiological data from the patient and to deliver therapy in response to the acquired data. The system for classifying events according to an embodiment of the present invention may also be in other medical devices, such as a cardiomyostimulator, a drug delivery system, cardiac and other physiologic monitors, electrical stimulators including nerve, muscle, and deep brain stimulators, cochlear implants, and heart assist IMDs or pumps, etc.

The data acquired by the implantable medical device 220 can be monitored by an external system, such as the access device 240, comprising a programming head 122, which remotely communicates with the implantable medical device 220. The programming head 122 is utilized in accordance with medical device programming systems known to those skilled in the art having the benefit of the present disclosure, for facilitating two-way communication between the implantable medical device 220 (e.g., pacemaker) and the access device 240. In this way, the classification of cardiac events according to an embodiment of the present invention may take place in the access device 240 once the required data is transmitted from the medical device 220 to the access device 240. Access device 240 may be located at a remote location relative to the patient and therefore the classification of events according to an embodiment of the present invention may be performed in the access device 240 once the required data has been transmitted from the medical device 220 to the access device 220 via the internet, for example.

The implantable medical device 220 is housed within a hermetically sealed, biologically inert outer canister or housing 113, which may itself be conductive so as to serve as an electrode in the implantable medical device 220 pacing/sensing circuit. One or more leads, collectively identified with reference numeral 114 in FIG. 1, are electrically coupled to the implantable medical device 220 and extend into the patient's heart 116 via a vein 118. Disposed generally near a distal end of the leads 114 are one or more exposed conductive electrodes (sensor/therapy delivery device 210) for receiving electrical cardiac signals or delivering electrical pacing stimuli to the heart 116. The leads 114 may be implanted with their distal end situated in either the atrium or ventricle of the heart 116. In an alternative embodiment, the sensor/therapy delivery device 210, or the leads 114 associated with the sensor/therapy delivery device 210, may be situated in a blood vessel on the heart 116, such as a vein 118.

Figure 2:
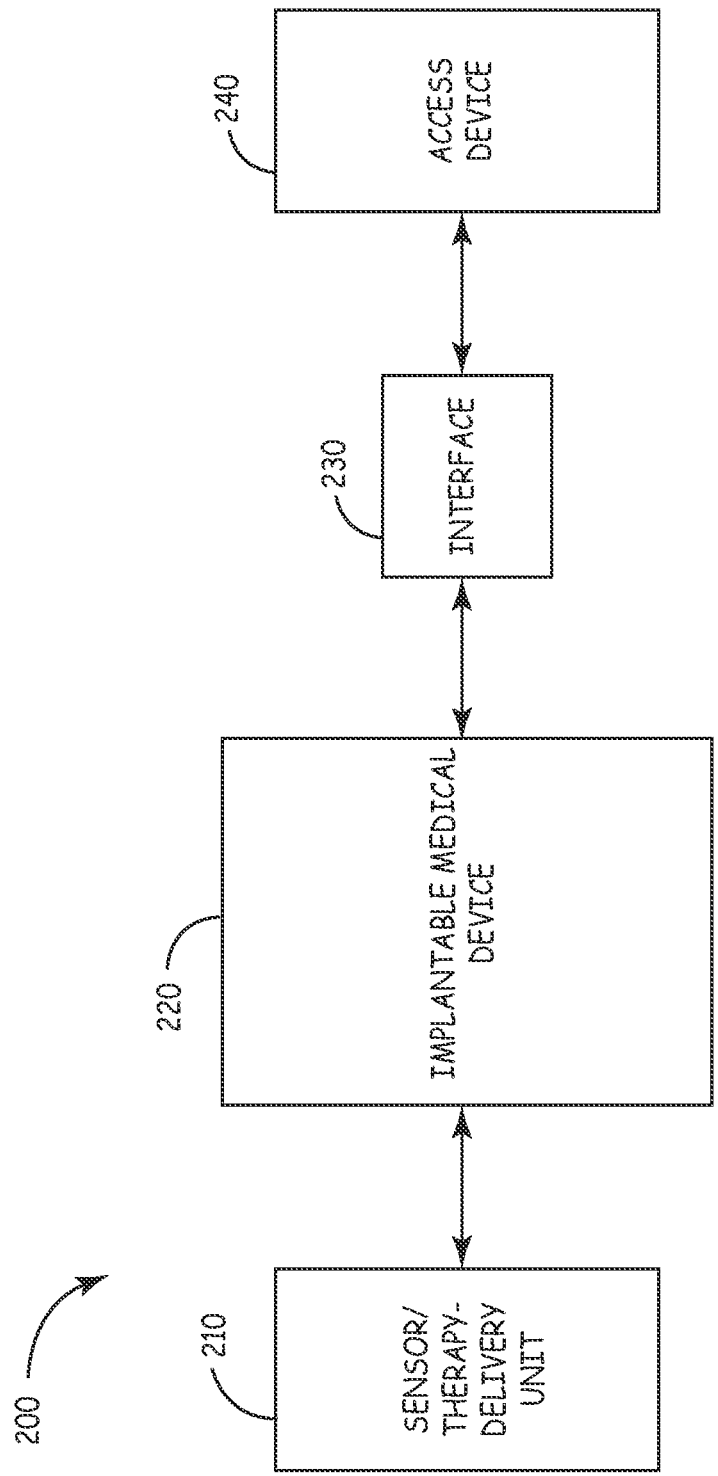
FIG. 2 is a schematic diagram of a system for classifying an event according to an embodiment of the present invention.

FIG. 2 is a schematic diagram of a system for classifying an event according to an embodiment of the present invention. As illustrated in FIG. 2, a system 200 for evaluating a prior classification of an event includes a sensor/therapy delivery unit 210, an implantable medical device 220, and an access device 240. Embodiments of the present invention can provide one or more of a plurality of physiological data and non-physiological data from the sensor/therapy delivery unit 210 to the implantable medical device 220, which are then processed and stored in the implantable medical device 220. The sensor/therapy delivery unit 210 may include a plurality of sensors that are capable of acquiring physiological and non-physiological data. Based upon data from the sensor(s) 210 and other factors, the implantable medical device 220 may deliver a therapy to a portion of the patient's body 105, via the sensor/therapy delivery unit 210. The access device 240 can be used to re-classify identification of events by the device 220, using the methods described below, and may reprogram and/or make modifications to the operation of the implantable medical device 220 accordingly. In another embodiment of the present invention, the device 220 is used to re-classify prior identification of events by the device 220 using the methods described below.

Figure 3:
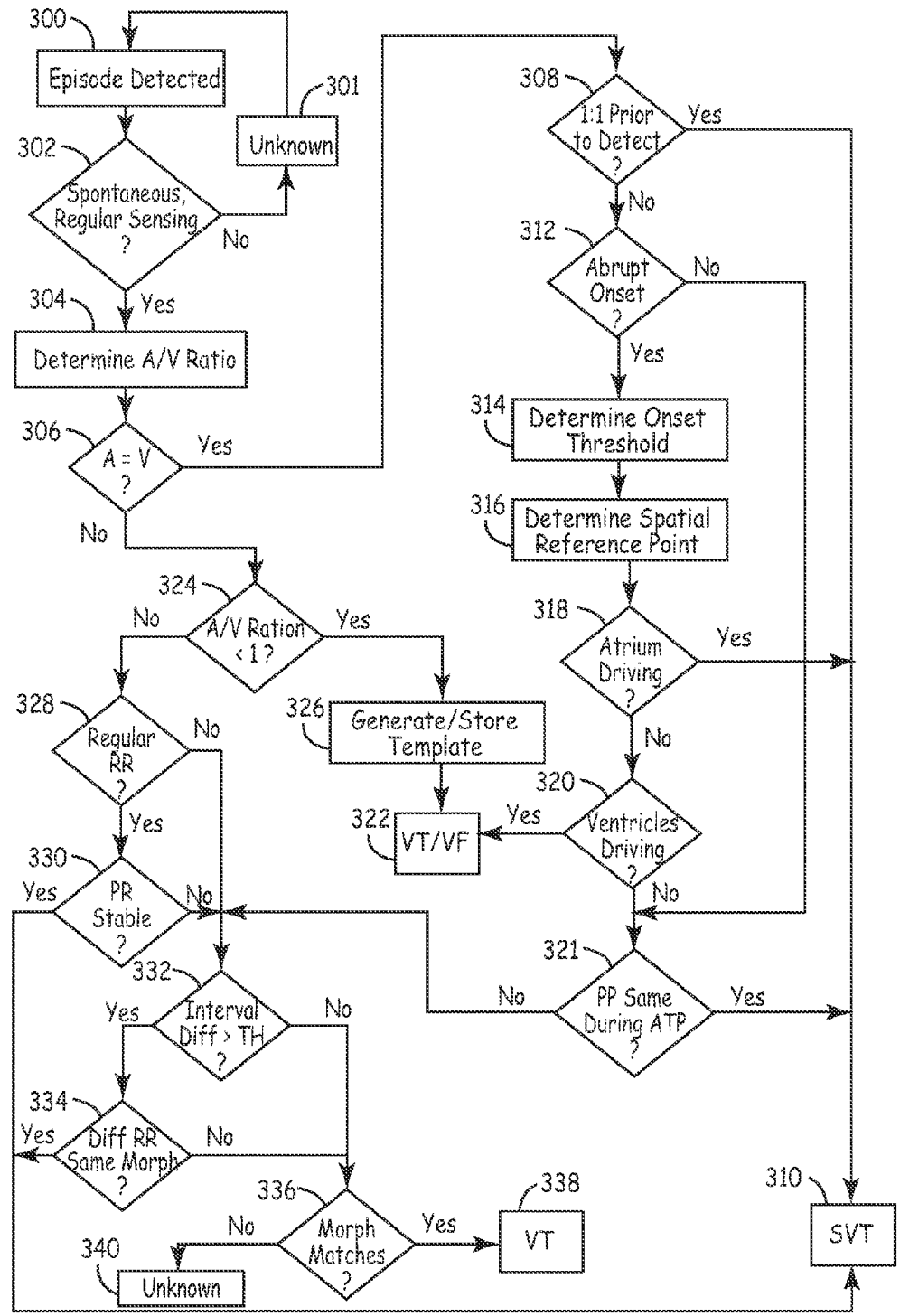
FIG. 3 is a flowchart of classifying of a cardiac event according to an embodiment of the present invention.

FIG. 3 is a flowchart of classifying of a cardiac event according to an embodiment of the present invention. The present invention relates to a method and apparatus for evaluating prior classifications of events by the device 220 that includes determining instances where an event was previously classified by the device as a detected event Block 300, such as ventricular fibrillation of ventricular tachycardia, for example. A determination is made as to whether the classification of the event as a detected event was made based on accurate sensing data. For example, a determination is made as to whether data associated with atrial sensing during the original classification of the event included the correct identification of atrial depolarizations that are both regular and spontaneous, i.e., not induced, Block 302. A detailed description of identification of atrial depolarizations that are regular and spontaneous, according to an embodiment of the present invention, is set forth below in reference to FIGS. 9-11.

Figure 4:
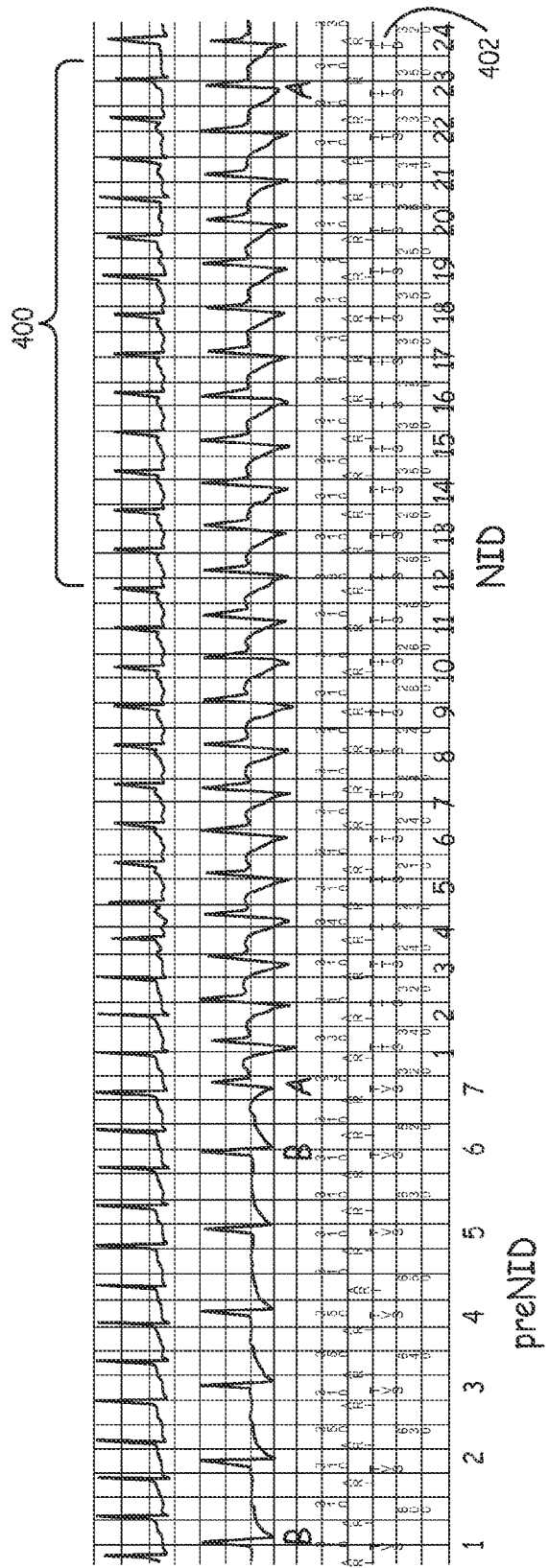
FIG. 4 is a graphical illustration of a determination of an A/V ratio during re-classification of a detected event according to an embodiment of the present invention.

If the atrial sensing is not determined to be both spontaneous and regular, No in Block 302, the detected event is marked as being unknown, Block 301, and the next event that was previously identified by the device as a detected episode is identified, Block 300. Once the atrial sensing is determined to be both spontaneous and regular, Block 302, the detected event is verified by being re-classified as either a supraventricular tachycardia event or a VT/VF event. According to an embodiment of the present invention, this re-classification of the detected event is made by determining an A/V ratio associated with the ratio of atrial sensed events to ventricular sensed events over a predetermined window of sensed events occurring prior to the detection of the event, Block 304. For example, as illustrated in FIG. 4, a predetermined window 400 utilized for calculating the A/V ratio may be defined by the last 12 ventricular sensed events $V_S$ occurring just prior to the point of the detection of the event 402, although it is understood that the window 400 may be defined by any predetermined number of ventricular sensed events $V_S$ prior to detection. The number of atrial sensed events $A_S$ occurring within the window 400 are then determined, and utilized to determine the A/V ratio. In the example of FIG. 4, fourteen atrial sensed events $A_S$ occur within the window 400.

If the number of atrial sensed events $A_S$ occurring during the window 400 is equal to the number of ventricular sensed events $V_S$ and therefore the A/V ratio is equal to one, Yes in Block 306, a determination is made in FIG. 3 as to whether the atrial sensed events $A_S$ are evenly distributed with the ventricular sensed events $V_S$ in a one-to-one distribution, i.e., one A for each V), Block 308. For example, a determination is made as to whether there is only one atrial sensed event $A_S$ located between each adjacent pair of all of the ventricular sensed events $V_S$ available in the detected episode prior to the window 400. If the atrial sensed events $A_S$ are evenly distributed with the ventricular sensed events $V_S$ in a one-to-one distribution, Yes in Block 308, i.e., there is one atrial sensed event $A_S$ located between each adjacent pair of all of the ventricular sensed events $V_S$, the event is identified as being a supraventricular tachycardia event, Block 310. The rationale behind this decision is that a ventricular arrhythmia would have a shorter ventricular cycle length than the atrial cycle length at some point in the episode.

According to an embodiment of the present invention, during the determination as to whether the number of atrial sensed events $A_S$ occurring during the window 400 is equal to the number of ventricular sensed events $V_S$, the A/V ratio may be determined to be equal to one, Yes in Block 306, if the number of atrial sensed events is within a predetermined range of the number of ventricular sensed events, such as plus or minus one. In addition, during the determination in Block 308 as to whether the atrial sensed events $A_S$ are evenly distributed with the ventricular sensed events $V_S$ in a one-to-one distribution, a predetermined number of instances where there are more than one atrial sensed event between adjacent pairs of ventricular sensed events may be included. For example, a determination is made as to whether there is only one atrial sensed event $A_S$ located between each adjacent pair of the ventricular sensed events $V_S$ prior to the window 400 and less than a predetermined number of adjacent pairs of ventricular events, such as three, having two beats.

If the atrial sensed events $A_S$ are determined to be not evenly distributed with the ventricular sensed events $V_S$ in a one-to-one distribution, No in Block 308, a determination is made as to whether there was an abrupt onset associated with the detected event, Block 312.

Figure 5:
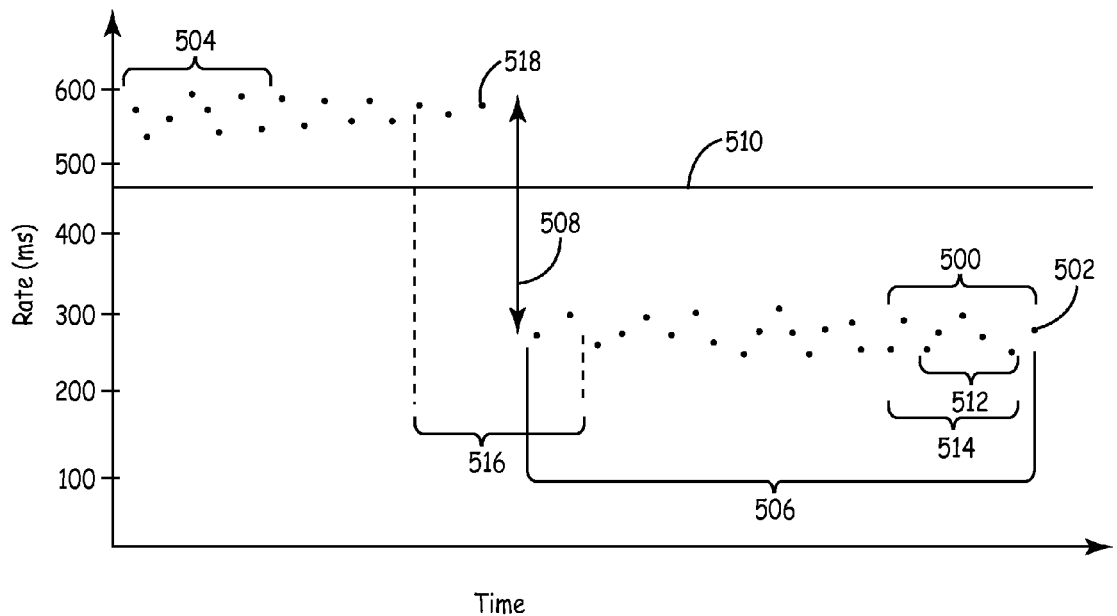
FIG. 5 is a graphical representation of determining whether there was an abrupt onset associated with a detected event according to an embodiment of the present invention.

FIG. 5 is a graphical representation of determining whether there was an abrupt onset associated with a detected event according to an embodiment of the present invention. As is known in the art, a cardiac event is detected once a predetermined number of intervals, commonly referred to as the number of intervals to detection (NID), having an interval rate that is less a predetermined detection rate have been detected. In the exemplary graphical representations of FIGS. 4 and 5, for example, the number of intervals to detection (NID) is 24 intervals. Therefore, during the initial detection process, the device 220 detects the occurrence of a cardiac event once the detection criteria have been met, i.e., once 24 intervals having a rate less than the threshold rate are detected.

As illustrated in FIG. 5, the determination of whether the onset of the event is abrupt is made by first determining the median of a predetermined number of detected intervals 500, such as eight detected intervals, for example, that occur just prior to an interval 502 corresponding to when the event is detected by the device as a cardiac event, along with the median of a predetermined number of detected intervals 504 occurring prior to the NID intervals 506 associated with prior detection of the event by the device 220 (at the beginning of the stored episode, for example). A difference 508 between the median of the predetermined number of detected intervals 500 and the median of the predetermined number of detected intervals 504 is determine, and the onset of the event is determined to be abrupt if the difference 508 between the medians is greater than a median difference threshold, such as 60 milliseconds, for example.

According to an embodiment of the present invention, the determination as to whether the onset of the event is an abrupt onset may be made using methods described in U.S. patent application Ser. No. 11/461,269, filed Mar. 29, 2006, to Stadler et al. incorporated herein by reference in it's entirety.

Returning to FIG. 3, if the difference 508 between the two medians is not greater than the median difference threshold, and therefore the onset of the event is determined not to be an abrupt onset, No in Block 312, the event is identified as being unable to be evaluated and the process continues with a next post-processing determination of the accuracy of the classification of the event, such as Block 321 for example, described below. If the difference 508 between the two medians is greater than the median difference threshold, and therefore the onset of the event is determined to be an abrupt onset, Yes in Block 312, the accuracy of the classification of the event is further evaluated by determining whether the heart rhythm is being initiated by conduction in either the ventricles or in the atrium. For example, according to an embodiment of the present invention, an onset threshold 510 is determined, Block 314, as the sum of the median of the predetermined number of detected intervals 500 occurring just prior to the interval 502 associated with detection of the event and a portion of the difference 508 between the two medians, set forth by the following equation:

$$\text{Onset Threshold} = \text{episode median} + X * \text{median difference} \quad \text{Equation 1}$$

where the episode median is the median of the predetermined number of events 500 occurring just prior to the interval 502 associated with detection of the event, the median difference is the difference 508 between the two medians, and X*median difference corresponds to a portion of the difference 508 between the two medians. According to one embodiment of the present invention, X is equal to two thirds, so that X*median difference corresponds to two thirds of the median difference.

Once the onset threshold 510 has been determined, Block 314, a spatial reference point is identified in Block 316 that is utilized to form a window for determining whether conduction of the heart rhythm is being initiated by one of the atrial and the ventricular chambers. For example, according to an embodiment of the present invention, an RR-interval associated with pre-NID or sinus rhythm, i.e., greater than the onset threshold 510, occurring prior to the interval 502 corresponding to when the event is determined to be detected, is identified and utilized as a spatial reference point for forming the window.

Using the example of FIG. 5, starting with and working backward in time from the interval 502 corresponding to detection of the event, the identification of the spatial reference point is made by determining when a predetermined number of sequential adjacent intervals occurring prior to interval 502 are greater than the onset threshold 510. For example, according to an embodiment of the present invention, a determination is made as to whether three intervals of five sequential adjacent intervals 512 occurring just prior to interval 502 are greater than the onset threshold 510. If three intervals of the window of five sequential adjacent intervals 512 (including interval 502) are not greater than the onset threshold 510, a determination is made as to whether three intervals of the next window of five adjacent intervals 514, working backward in time from the interval 502 corresponding to detection of the event, are greater than the onset threshold 510. The process continues until an interval is identified where three intervals of a window 516 of five intervals are greater than the onset threshold 510.

Once window 516 is identified, the interval 518 of window 516 that is greater than the onset threshold 510 and closest to the interval 502 corresponding to detection of the event is set as the spatial reference point for forming the window for determining whether conduction of the heart rhythm is being initiated by one of the atrial and the ventricular chambers.

Figure 6A:
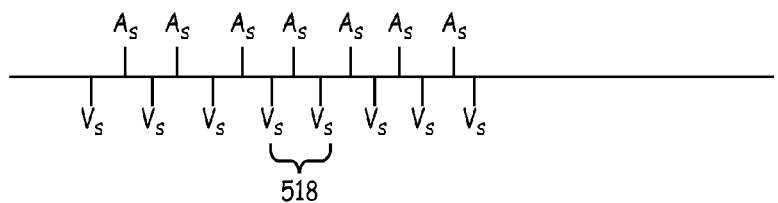
FIGS. 6A-6C are graphical representations of determining whether there is a leading chamber according to an embodiment of the present invention.
Figure 6B:
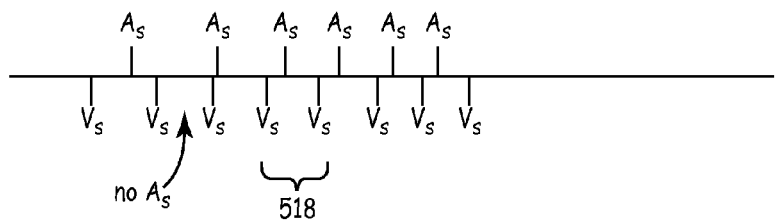
Figure 6C:
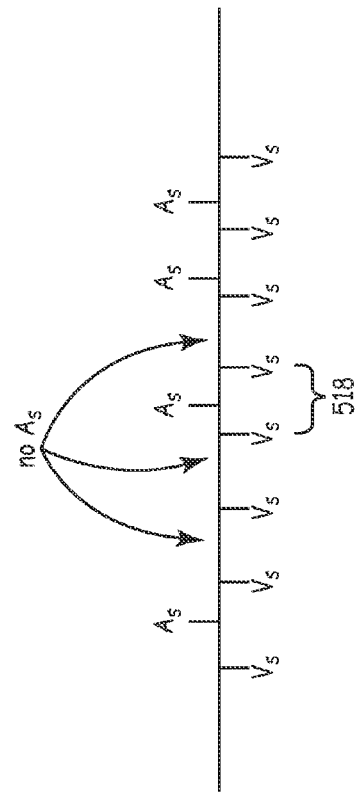

FIGS. 6A-6C are graphical representations of determining whether there is a leading chamber according to an embodiment of the present invention. Using a predetermined number of intervals centered around the determined spatial reference point, i.e., interval 518, the number sensed atrial events that occur between each interval is determined, the results of which are then utilized to determine whether conduction of the heart rhythm is being initiated by one of the atrial chamber, Block 318, and the ventricular chamber, Block 320. For example, as illustrated in FIGS. 6A and 6B, using three intervals centered around interval 518, a determination is made as to the number of atrial sensed events that occur between the resulting seven intervals.

If, as illustrated in FIG. 6A, there is one atrial sensed event $A_s$ between each of the adjacent ventricular sensed events $V_s$ forming the seven intervals, the atrium is determined to be initiating conduction, Yes in Block 318, and the event is identified as being a supraventricular tachycardia event, Block 310. If, as illustrated in FIG. 6B, there is one atrial sensed event $A_s$ between each of the adjacent ventricular sensed events $V_s$ for six of the seven intervals and no atrial sensed event $A_s$ between adjacent ventricular sensed events $V_s$ for one of the intervals, the ventricles are determined to be initiating conduction, Yes in Block 320, and the event is classified as being a VT/VF event, Block 322. Finally, if, as illustrated in FIG. 6C, there is one atrial sensed event $A_s$ between each of the adjacent ventricular sensed events $V_s$ for less than six of the seven intervals, and no atrial sensed event $A_s$ between adjacent ventricular sensed events $V_s$ for more than one of the intervals, then neither the atrium nor the ventricles are determined to be driving conduction, No in Blocks 318 and 320, and a determination is made as to whether the effects of antitachycardia pacing are indicative of a supraventricular tachycardia event, Block 321 of FIG. 3.

According to an embodiment of the present invention, the determination as to whether the effects of antitachycardia pacing are indicative of a supraventricular tachycardia event, Block 321, are made utilizing the method of dynamic discrimination described in commonly assigned U.S. patent application Ser. No. 10/839,634, filed May 5, 2004, and entitled "DYNAMIC DISCRIMINATION UTILIZING ANTI-TACHY PACING THERAPY IN A/V IMPLANTABLE MEDICAL DEVICE", incorporated herein by reference in it's entirety. For example, instances where the device 220 delivered an antitachycardia pcing regimen are identified, and the EGMs associated with the therapy are reviewed by determining a mean cycle length between atrial events occurring prior to the delivery of the antitachycardia pacing therapy and comparing the determined mean atrial cycle length with an atrial cycle length during the delivery of the pacing therapy. If the difference between the mean atrial cycle and the atrial cycle length during the delivery of the pacing therapy is less than or equal to a predetermined atrial cycle length threshold, such as 30 ms for example, the event is re-classified as being a supraventricular tachycardia event, Block 310. If the difference between the mean atrial cycle length and the atrial cycle length during the delivery of the pacing therapy is greater than the predetermined atrial cycle length threshold, the minimum interval (during NID intervals associated with detection of the event) and the maximum interval of all intervals are identified and a determination is made as to whether the difference between the maximum interval and the minimum interval is greater than a predetermined threshold, such as 100 ms for example, Block 332.

If the difference between the maximum interval and the minimum interval is not greater than a predetermined threshold, No in Block 332, the morphologies of each of the intervals associated with the detecting of the event are compared with the template or templates stored in Block 326, and a determination is made for each as to whether the correlation of the morphology is greater than a predetermined correlation threshold, such as 0.95 for example. A determination is made as to whether the number of intervals that correlate with the stored threshold is greater than a predetermined matching percentage threshold, such as 80% for example, Block 336.

If the difference between the maximum interval and the minimum interval is greater than the predetermined threshold, Yes in Block 332, the morphology of the maximum interval is compared with the morphology of the minimum interval, and a determination is made as to whether the correlation of the maximum interval with the minimum interval is greater than a predetermined correlation threshold, Block 334, such as 0.94 for example.

If the correlation of the maximum interval with the minimum interval is greater than the predetermined correlation threshold, Yes in Block 334, the detected event is re-classified as being a supraventricular tachycardia, Block 310. If the correlation of the maximum interval with the minimum interval is not greater than the predetermined correlation threshold, No in Block 334, the morphologies of each of the intervals associated with the detecting of the event are compared with the template or templates stored in Block 326, and a determination is made for each as to whether the correlation of the morphology is greater than a predetermined correlation threshold, such as 0.95 for example. A determination is made as to whether the number of intervals that correlate with the stored template is greater than a predetermined matching percentage threshold, Block 336, such as 80% for example.

According to an embodiment of the present invention, either a single template or more than one template may be stored, such as four for example, with each of the stored templates being utilized in the re-classification of detected events as described below. In addition, the stored templates may be generated from any episode from the same patient, either during the analysis of the current save to disk or across different interrogations.

If the number of intervals, having morphologies that are determined to have a correlation with the stored template that is greater than the correlation threshold, is greater than the predetermined matching percentage threshold, Yes in Block 336, the previously detected event is re-classified as being a ventricular tachycardia event, Block 338. If the number of intervals having morphologies 80 that are determined to have a correlation with the stored template that is greater than the correlation threshold is not greater than the predetermined matching percentage threshold, No in Block 336, a re-classification of the detected event is not possible, and therefore the previously detected event is identified as being unknown, Block 340.

If the number of atrial sensed events $A_S$ occurring during the window 400 is not equal to the number of ventricular sensed events $V_S$ and therefore the A/V ratio is not equal to one, No in Block 306, a determination is made in Block 324 as to whether the number of ventricular sensed events $V_S$ is greater than the number of atrial sensed events $A_S$ and therefore the A/V ratio is less than one. If the number of ventricular sensed events $V_S$ is greater than the number of atrial sensed events $A_S$ and therefore the A/V rate is less than one, Yes in Block 324, a template is generated and stored, Block 326, and the event is classified as a VT/VF event, Block 322.

Figure 7:
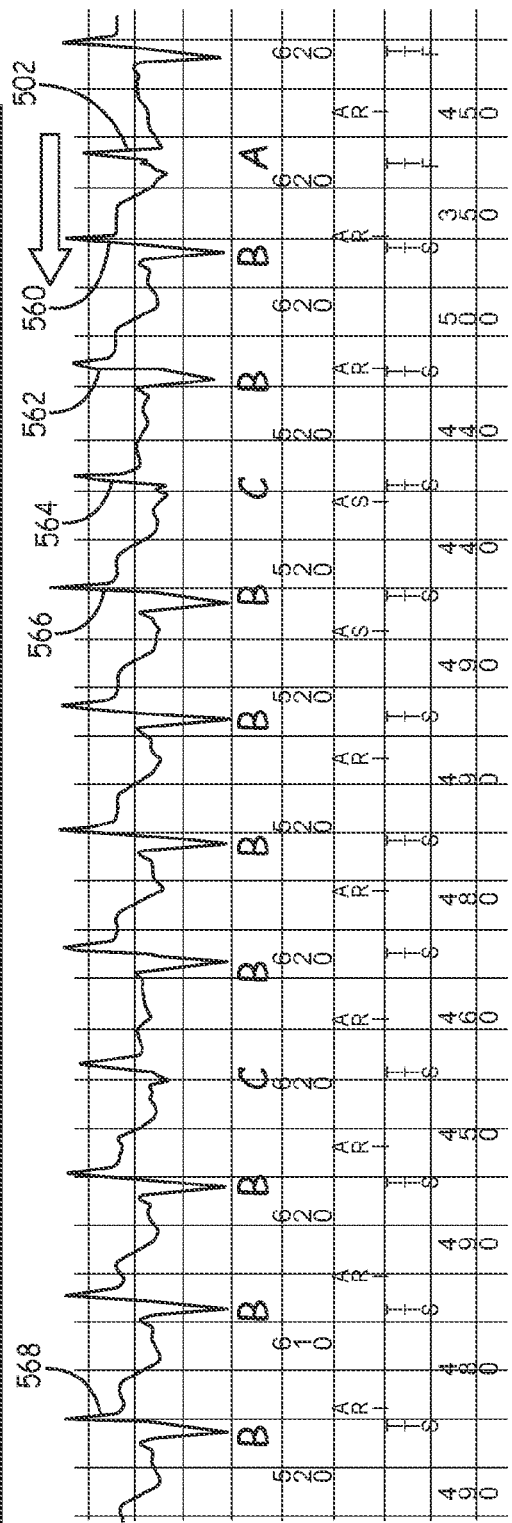
FIG. 7 is a graphical illustration of generation of a template according to an embodiment of the present invention.

FIG. 7 is a graphical illustration of generation of a template according to an embodiment of the present invention. As illustrated in FIG. 7, according to an embodiment of the present invention, in order to generate the template in Block 328, the present invention correlatives the morphology of adjacent intervals, starting with and working backward in time from the interval 502 associated with detection of the event. For example, a morphology of the interval 502 is determined and identified by a template, i.e., template A in FIG. 7. The morphology of an interval 560 occurring just prior and adjacent to interval 502 is compared with template A, and if the morphology of interval 560 has a predetermined correlation with the morphology of interval 502, such as a correlation that is greater than or equal to 0.82, for example, then the two intervals are identified as being correlated and interval 560 is identified by template A. If the morphologies do not correlate, i.e., have a correlation less than 0.82, then the morphology of interval 560 is identified by a new template, template B in FIG. 7.

Once the correlation of intervals 502 and 560 have been determined and the morphologies are identified by a template, a determination is made as to whether the morphology of a next interval 562, occurring just prior to the most recently correlated interval, interval 560, correlates with one of the previously generated templates, i.e., template A or template B. In particular, in the example of FIG. 7, since the correlation of interval 562 with template B is equal to 0.98 and the correlation of interval 562 with template A is equal to 0.72, interval 562 is determined to correlate with template B (0.98 is greater than 0.82) but not with template A (0.72 is not greater than or equal to 0.82). As a result, the morphology of interval 562 is identified as having the same morphology as template B.

Once the correlation of interval 562 with the previously generated templates is completed and interval 562 has been identified with a template, a determination is made as to whether the morphology of a next interval 564, occurring just prior to the most recently correlated interval, interval 562, correlates with one of the previously generated templates, i.e., template A or template B. In particular, in the example of FIG. 7, since the correlation of interval 564 with template B is equal to 0.80 and the correlation of interval 564 with template A is equal to 0.81, interval 564 is determined not to correlate with template B (0.80 is less than 0.82) or with template A (0.81 is less than 0.82). As a result, the morphology of interval 562 is identified as having a different morphology and is therefore a new template C is generated based on the morphology of interval 564 and the morphology of interval 564 is identified as having the same morphology as new template C.

Once the correlation of interval 564 with the previously generated templates is completed and interval 564 has been identified with a template, a determination is made as to whether the morphology of a next interval 566, occurring just prior to the most recently correlated interval, interval 565, correlates with one of the previously generated templates, i.e., template A, template B or template C. In particular, in the example of FIG. 7, since the correlation of interval 566 with template C is equal to 0.82, the correlation of interval 566 with template B is equal to 0.99 and the correlation of interval 566 with template A is equal to 0.69, interval 566 is determined to be correlated with template C (0.82 is greater than or equal to 0.82) and template B (0.99 is greater than 0.82), but not with template A (0.69 is less than 0.82). Since the morphology of interval 566 is identified as having the same morphology as template B and template C, a determination is made as whether the correlation of template interval 566 is with template B is greater than the correlation of template interval 566 with template C. Since the correlation between interval 566 and template B is greater than the correlation between interval 566 and template C, the morphology of interval 566 is identified as having the same morphology as template B. On the other hand, if the correlation between interval 566 and template B was greater than the correlation between interval 566 and template C, the morphology of interval 566 would be identified as having the same morphology as template C.

The process is repeated for the remainder of the twelve intervals, with the morphology of each interval either being identified with one of the previously generated templates, either the highest of multiple determined correlated templates, or with the single correlated template, or with a new template based on the current interval, so that, returning to FIG. 3, once the final interval 568 is identified with a template, the generated template that is correlated with the greatest number of intervals (template B in the example of FIG. 7) is set as the template associated with the detected event in and is stored in memory Block 326. In addition, the generated template that is correlated with the greatest number of intervals must also include a predetermined percentage, such as 80% for example, of all of the intervals utilized. The event is then classified as being a VT/VF event Block 322.

If the number of atrial sensed events $A_S$ occurring during the window 400 is greater than the number of ventricular sensed events $V_S$, and therefore the A/V ratio is neither equal to one, No in Block 306, nor less than one, No in Block 324, a determination is made as to whether the data utilized by the device during the initial classification of the event as a detected event includes intervals that are regular, Block 328.

Figure 8:
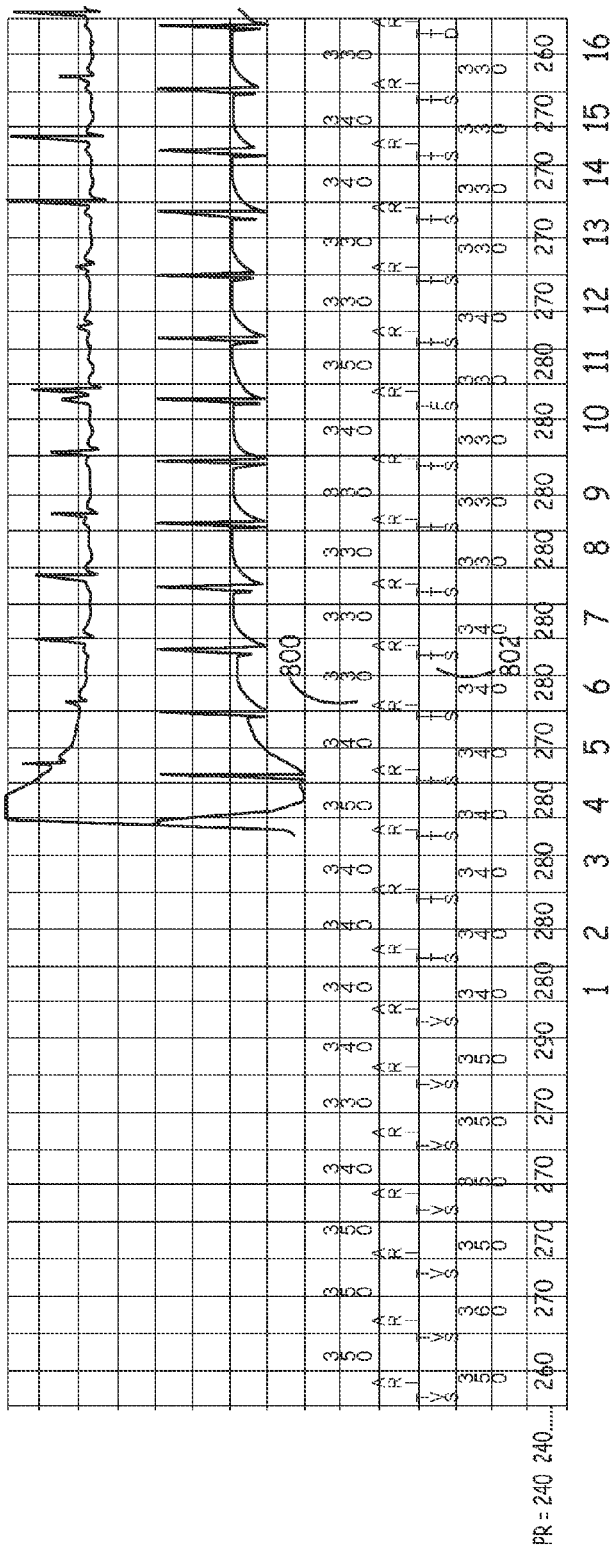
FIG. 8 is a graphical representation of exemplary data utilized in the classification of an event by an implantable medical device.

FIG. 8 is a graphical representation of exemplary data utilized in the classification of an event by an implantable medical device. In the exemplary graphical representation of FIG. 8, the number of intervals to detection (NID) is 16 intervals. Therefore, during the initial detection process, the device 220 has detected the occurrence of a cardiac event once the detection criteria have been met, i.e., once 16 intervals having a rate less than the threshold rate are detected. According to an embodiment of the present invention, in order to determine whether the data utilized by the device during the initial classification of the event as a detected event includes intervals that are regular, a modesum of the 16 RR intervals resulting in detection is generated by determining whether the number of intervals in the two highest modes (i.e., most frequent bins) is greater than a predetermined percentage of the number of RR intervals, such as 67% for example. In particular, in the exemplary data illustrated in FIG. 8, since the two most frequent bins both include eight of the sixteen intervals at interval lengths of 330 ms and 340 ms, the modesum is 100% and therefore greater than the predetermined percentage of the number of RR intervals. Therefore, the RR intervals are determined to be regular, Yes in Block 328.

If the RR intervals are determined not to be regular, No in Block 328, the event is identified as being unable to be evaluated and the process continues with a next post-processing determination of the accuracy of the classification of the event, such as Block 332 for example, described below. On the other hand, if the RR intervals are determined to be regular, Yes in Block 328, a determination is made as to whether the A/V intervals associated with the initial identification of the event as a cardiac event are stable, Block 330. For example, according to an embodiment of the present invention, in order to determine whether the A/V intervals associated with the initial identification of the event as a cardiac event are stable, PR intervals, i.e., the time between an atrial sense 800 and a subsequent ventricular sense 802, are determined for each of the intervals associated with the initial identification of the event as a cardiac event are determined.

In order to reduce the effect of outliers, once the PR intervals are determined for each of the intervals associated with the initial identification of the event as a cardiac event, a predetermined number maximum PR intervals and the minimum PR intervals are removed. For example, according to an embodiment of the present invention, one sixth of the maximum PR intervals and one sixth of the minimum PR intervals are removed. A PR range is then determined as the difference between the minimum PR interval and the maximum PR interval, and a determination is made as to whether a range of the PR intervals satisfies a PR stable criteria. For example, for the data of FIG. 8, a determination is made as to whether the range of the remaining PR intervals is less than 20 ms.

In the example of FIG. 8, once the minimum and the maximum intervals were removed, the PR range is 10 ms, and therefore the range of the PR intervals is determined to less than 20 ms.

If the range of the PR intervals is determined to less than or equal to 20 ms and therefore the A/V intervals associated with the initial identification of the event as a cardiac event are stable, Yes in Block 330, the event is re-classified as being a supraventricular event, Block 310. On the other hand, if the range of the PR intervals is determined to be greater than 20 ms and therefore the A/V intervals associated with the initial identification of the event as a cardiac event are not stable, No in Block 330, the minimum interval and the maximum interval of the NID intervals associated with the detection of the event are identified and a determination is made as to whether the difference between the maximum interval and the minimum interval is greater than a predetermined threshold, such as 100 ms for example, Block 332.

If the difference between the maximum interval and the minimum interval is not greater than a predetermined threshold, No in Block 322, the event is identified as being unable to be evaluated and the process continues with a next post-processing determination of the accuracy of the classification of the event, such as Block 336, described below. If the difference between the maximum interval and the minimum interval is greater than the predetermined threshold, Yes in Block 332, the morphology of the maximum interval is compared with the morphology of the minimum interval, and a determination is made as to whether the correlation of the maximum interval with the minimum interval is greater than a predetermined correlation threshold, Block 334, such as 0.94 for example.

If the correlation of the maximum interval with the minimum interval is not greater than the predetermined correlation threshold, No in Block 334, the detected event is re-classified as being a supraventricular tachycardia, Block 310. If the correlation of the maximum interval with the minimum interval is greater than the predetermined correlation threshold, Yes in Block 334, the morphologies of each of the intervals associated with the detecting of the event are compared with the template or templates stored in Block 326, and a determination is made for each as to whether the correlation of the morphology is greater than a predetermined correlation threshold, such as 0.95 for example. A determination is made as to whether the number of intervals that correlate with the stored threshold is greater than a predetermined matching percentage threshold, such as 80% for example.

If the number of intervals having morphologies 80 that are determined to have a correlation with the stored template that is greater than the correlation threshold is greater than the predetermined threshold, Yes in Block 336, the previously detected event is re-classified as being a ventricular tachycardia event, Block 338. If the number of intervals having morphologies 80 that are determined to have a correlation with the stored template that is greater than the correlation threshold is not greater than the predetermined threshold, No in Block 336, a re-classification of the detected event is not possible, and therefore the previously detected event is identified as being unknown, Block 340.

In this way, by enabling review and post-processing of each detected event, the present invention reduces the time required by a clinician or other medical personnel to review the accuracy of classification of episodes by the device in order to identify inappropriate detections, and also decreases the likelihood that time is spent reviewing detections unnecessarily. In addition, as less experienced medical personal review the episodes stored in the memory of an implantable medical device, the process of the present application will provide an increased likelihood that a correct classification will be made.

Figure 9:
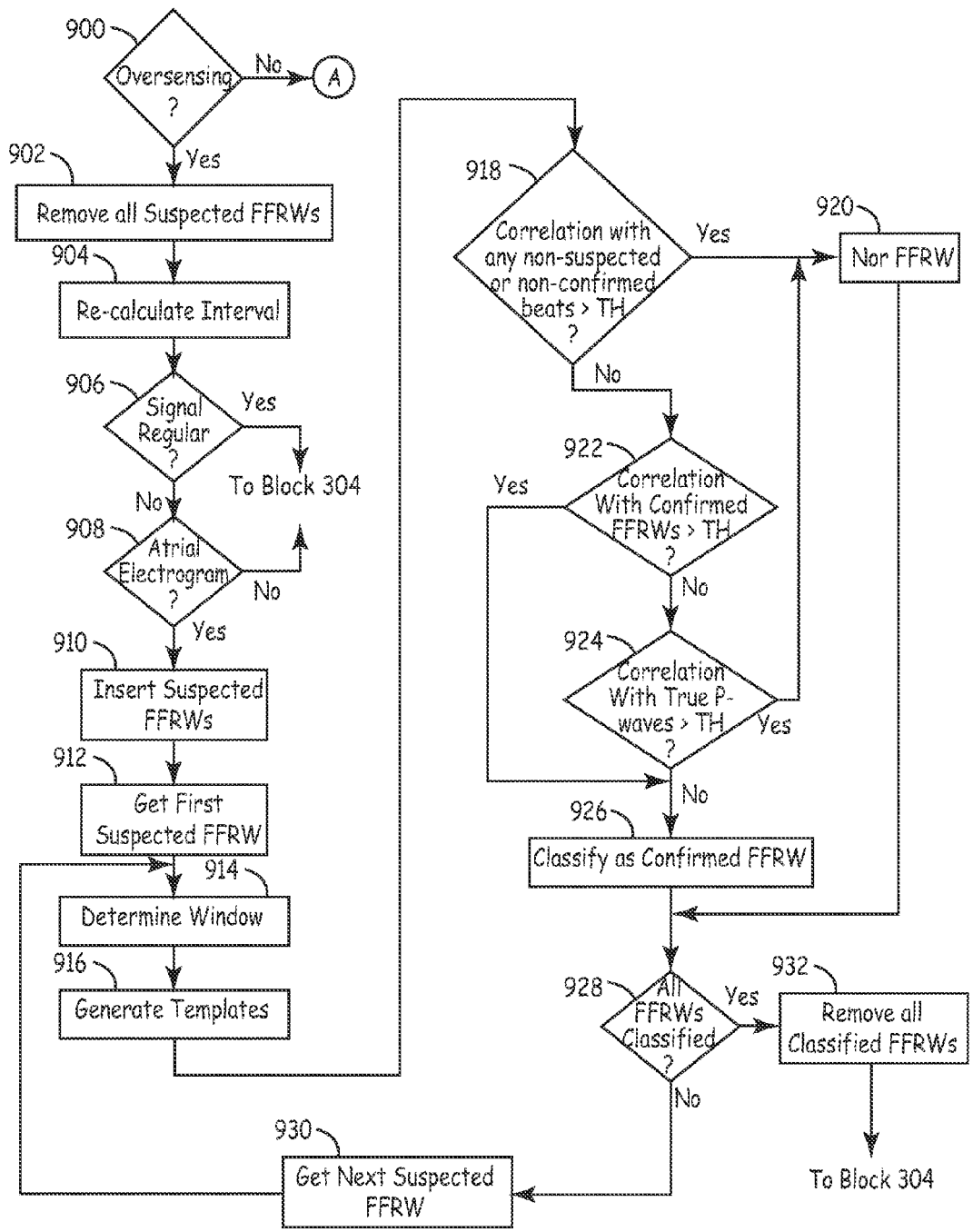
FIG. 9 is a flowchart of a method of determining whether data previously utilized by a device to identify a cardiac event corresponds to regular sensing of events by the device according to an embodiment of the present invention.
Figure 10:
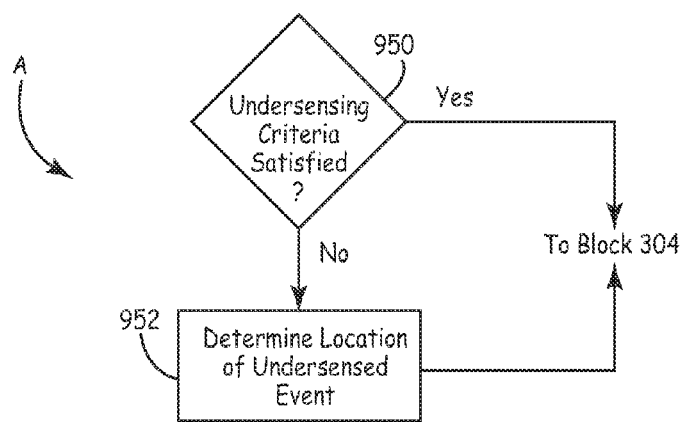
FIG. 10 is a flowchart of a method of determining whether data previously utilized by a device to identify a cardiac event corresponds to regular sensing of events by the device according to an embodiment of the present invention.

FIG. 10 is a graphical illustration of determining whether atrial sensed events are evenly distributed with the ventricular sensed events according to an embodiment of the present invention. As illustrated in FIG. 10, according to an embodiment of the present invention, during the determination as to whether the atrial sensed events $A_S$ are evenly distributed with the ventricular sensed events $V_S$ in Block 308, FIG. 9 is a flowchart of a method of determining whether data previously utilized by a device to identify a cardiac event corresponds to regular sensing of events by the device according to an embodiment of the present invention. As illustrated in FIG. 9, according to an embodiment of the present invention, during the determination as to whether the atrial sensing is both spontaneous and regular in Block 302, retrieved stored data associated with prior classifications of events by the device 220 is reviewed by the access device 240 to identify whether there are instances where oversensing is suspected to have occurred, Block 900. For example, a determination is made by the access device 240 as to whether oversensing is suspected to have occurred in Block 900 by determining whether there are instances where the device 220 has identified the existence of far-field R-waves (FFRWs) that have been identified by the device 220 as atrial sensed events, using known detection algorithms, such as those described in U.S. Pat. No. 6,178,350 to Gillberg et al., U.S. Pat. No. 6,052,620 to Gillberg et al., and U.S. Pat. No. 5,755,736 to Gillberg et al., for example, incorporated herein by reference in their entireties. The R-waves that were identified by the device 220 as far-field R-waves are then classified by the access device 240 as being suspected far-field R-waves.

In addition, other factors that are utilized by the access device 240 to identify suspected far-field R-waves in Block 900 may include those instances of far-field R-waves that are located after the period of detection by the device 220, instances of simultaneous atrial and ventricular events, except in instances where the ventricular event is TP (Ventricular Pace for ATP), and instances where a predetermined number of PP intervals, such as four for example, are determined to be stable when a suspected far-field R-wave(s) in that period of true PP intervals are ignored. According to an embodiment of the present invention, PP intervals are also considered to be stable if each value of the predetermined number of PP intervals is within a predetermined range, such as less than or equal to 110% and greater than or equal to 91%, for example.

Once the suspected far-field R-waves have been identified, Yes in Block 900, using the techniques described above, all of the determined suspected far-field senses are removed, Block 902, and the intervals are re-calculated without the suspected far-field R-wave, Block 904. A determination is then made as to whether the signal having the suspected far-field R-waves removed is regular, Block 906. According to an embodiment of the present invention, in order to determine whether the signal having the suspected far-field R-waves removed is regular, a modesum of the signals starting with and working backward in time from the interval corresponding to detection of the event by the device 220 is generated by the access device 240, and a determination is made as to whether the modesum is greater than or equal to 99%.

If the signal having the suspected far-field R-waves removed is determined to be regular, i.e., the modesum is greater than or equal to 99%, Yes in Block 906, the signal is determined to be spontaneous and regular, Yes in Block 302 of FIG. 3, and the process continues with the determination of the A/V ratio, Block 304 of FIG. 3 as described above. If the signal having the suspected far-field R-waves removed is determined to not be regular, i.e., the modesum is not greater than or equal to 99%, No in Block 906, a determination is made as to whether the data received from the device 220 by access device 240 includes an atrial electrogram, Block 908. If the data received from the device 220 by access device 240 does not include an atrial electrogram, No in Block 908, such information is stored by the access device 240, and the signal is determined to be spontaneous and regular, Yes in Block 302 of FIG. 3, and the process continues with the determination of the A/V ratio, Block 304 of FIG. 3 as described above.

If the data received from the device 220 by access device 240 does include an atrial electrogram, Yes in Block 908, the suspected far-field R-waves that were removed in Block 902 are inserted back within the signal, Block 910, and the first suspected far-field R-wave prior to the point of detection of the event by the device 220 is identified, Block 912. A window of sensed beats is then formed about the suspected far-field R-wave, Block 914, using a predetermined number of beats subsequent to and prior to the far-field R-wave. For example, according to an embodiment of the present invention, the window of Block 914 includes 10 sensed beats, including six beats prior to the suspected far-field R-wave and three beats subsequent to the suspected far-field R-wave (i.e., the far-field R-wave is the seventh of ten beats). Once the window is determined in Block 914, a template is generated corresponding to the morphology of each of the intervals in the window, Block 916, and a determination is made as to whether the morphology of the suspected far-field R-wave has a predetermined correlation, such as 0.92 for example, with an interval in the window that is a non-suspected and non-confirmed beat, Block 918.

If the morphology of the current suspected far-field R-wave is determined to have the predetermined correlation with an interval in the window that is a non-suspected and non-confirmed beat, Yes in Block 918, the current suspected far-field R-wave is classified as not being a far-field R-wave, Block 920. If the morphology of the current suspected far-field R-wave is determined not to have the predetermined correlation with an interval in the window that is a non-suspected and non-confirmed beat, No in Block 918, a determination is made as to whether the current suspected far-field R-wave has a predetermined correlation, such as 0.82 for example, with a predetermined number of previously confirmed far-field R-waves, such as 67% for example, Block 922.

If the current suspected far-field R-wave has the predetermined correlation with the predetermined number of previously confirmed far-field R-waves, Yes in Block 922, the current suspected far-field R-wave is classified as a confirmed far-field R-wave, Block 926. If there are no previously confirmed far-field R-waves or if the current suspected far-field R-wave does not has the predetermined correlation with the predetermined number of previously confirmed far-field R-waves, No in Block 922, a determination is made as to whether the current suspected far-field R-wave has the predetermined correlation with a predetermined number of true p-waves in the window (i.e., intervals that are neither suspected nor confirmed far-field R-waves), such as 67% for example, Block 924.

If the current suspected far-field R-waves has the predetermined correlation with the predetermined number of true p-waves, Yes in Block 924, the current suspected far-field R-wave is classified as not being a far-field R-wave, Block 920. However, if the current suspected far-field R-waves does not has the predetermined correlation with the predetermined number of true p-waves, No in Block 924, the current suspected far-field R-wave is classified as a confirmed far-field R-wave, Block 926.

Once the current suspected far-field R-wave is classified as a confirmed far-field R-wave, Block 926 or as not being a far-field R-wave, Block 920, a determination is made as to whether all of the suspected far-field R-waves have been classified by the access device 240, Block 928. If all of the suspected far-field R-waves have not been classified by the access device 240, No in Block 928, the next suspected far-field R-wave is located, Block 930, the window is determined as described above in Block 914 for the next far-field R-wave and the process is repeated. If all of the suspected far-field R-waves have been classified by the access device 240, Yes in Block 928, the classified far-field R-waves are removed from the signal, Block 932, the signal is determined to be spontaneous and regular, Yes in Block 302 of FIG. 3, and the process continues with the determination of the A/V ratio, Block 304 of FIG. 3 as described above.

According to an embodiment of the present invention, once the current suspected far-field R-wave is classified as a confirmed far-field R-wave, Block 926, this classification made be further verified by removing the classified far-field R-wave, re-calculating the resulting new A-A interval and determining whether the new A-A interval is less than an average of a predetermined number of previous A-A intervals by less than or equal to a predetermined threshold. For example, a determination is made as to whether the new A-A interval is 30 ms or less than an average of ten previous A-A intervals. If the new A-A interval is 30 ms or less than the average of ten previous A-A intervals, the classification of the interval as a confirmed far-field R-wave is confirmed. However, if the new A-A interval is not 30 ms or less than the average of ten previous A-A intervals, the classification is changed from being a confirmed far-field R-wave to being not a far-field R-wave. The process then continues by determining whether all of the suspected far-field R-waves have been classified by the access device 240, Block 928.

As illustrated in FIG. 9, if no suspected far-field R-waves were identified by the device 220 and therefore the access device 240 determines that oversensing is not suspected to have occurred, No in Block 900, a determination is made by the access device 240 as to whether undersensing has occurred, Block A. FIG. 10 is a flowchart of a method of determining whether data previously utilized by a device to identify a cardiac event corresponds to regular sensing of events by the device according to an embodiment of the present invention. As illustrated in FIG. 10, according to an embodiment of the present invention, the determination as to whether undersensing has occurred is made, for example, by determining whether one of a predetermined number of undersensing criteria have been met, Block 950. An examples of an undersensing criteria would include determining whether at least one sensed AA interval associated with predetermined beats, such as the NID ventricular beats prior to detection of the event and the atrial interval immediately subsequent to the detection of the event for example, greater than a predetermined interval, such as 2500 ms for example. Another example of an undersensing criteria would include determining whether the atrial channel includes less than a predetermined number of events, such as nine events for example, prior to detection.

Another example of an undersensing criteria according to the present invention would include calculating a median atrial interval in a sliding window of a predetermined number of intervals, such as eight intervals for example, and determining whether the median atrial interval is greater than a predetermined threshold, such as 1300 ms for example. If the median atrial interval is greater than the predetermined threshold, atrial undersensing is determined to have occurred, Yes in Block 950. Atrial undersensing is also determined to have occurred if the median is greater than a predetermined threshold, such as 350 ms for example and a current atrial interval, such as the final atrial event in the window for example, i.e., the eighth event, is greater than the median by a predetermined threshold, such as 1.7 times the median interval or more, for example. Atrial undersensing is also determined to have occurred if the median is within a predetermined range, such as greater than 200 ms and less than or equal to 359 ms for example, and a current atrial interval, such as the final atrial event in the window for example, i.e., the eighth event, is greater than the median by a predetermined threshold, such as 1.9 times the median interval or more, for example. Atrial undersensing may be determined to have occurred if the median is greater than 0 ms and less than or equal to 200 ms, and a current atrial interval, such as the final atrial event in the window for example, i.e., the eighth event, is greater than the median by a predetermined threshold, such as 3.25 times the median interval or more, for example.

Figure 11:
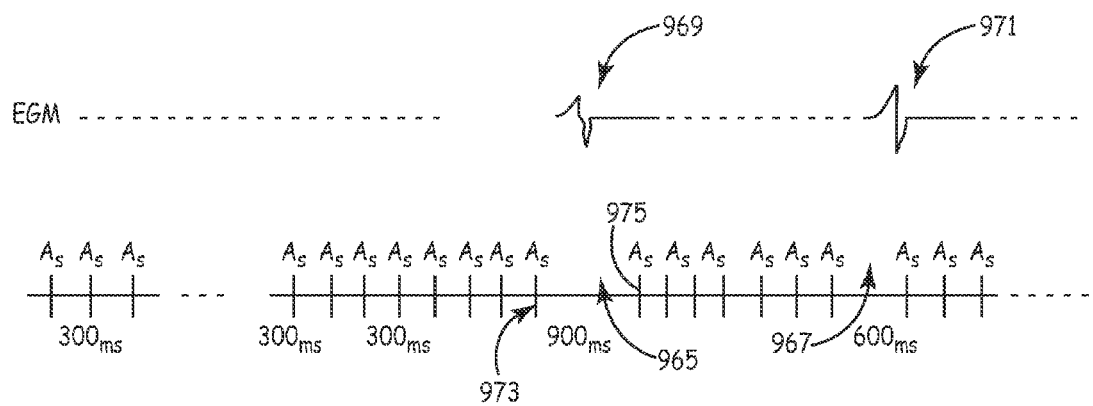
FIG. 11 is a graphical illustration of determining whether undersensing has occurred according to an embodiment of the present invention.

Another criteria for determining whether atrial undersensing has occurred, according to an embodiment of the present invention, includes determining whether there are two or less intervals in the entire record that are two times the median AA interval, or three times the median AA interval and a majority of the AA intervals are regular, and there is a depolarization on the atrial egm signal where the expected atrial event would have occurred. FIG. 11 is a graphical illustration of determining whether undersensing has occurred according to an embodiment of the present invention. For example, as illustrated in FIG. 11, regular AA intervals (approximately equal to 300 ms) are sensed for a majority of the sensed atrial events $A_s$, such as 92% for example, and there is only one or two depolarizations that are either an interval 965 that is 900 ms and therefore three times the median AA interval (300 ms), or an interval 967 that is 600 ms and therefore two times the median AA interval, and for each interval 965 and 967 there is an associated depolarization, 969 and 971 respectively, on the atrial EGM.

A final exemplary criteria for determining atrial undersensing has occurred includes determining whether a predetermined number of the AA intervals in the entire record are within a predetermined range of the median of the AA intervals, such as 92% within the range of the median, and there are less than or equal to four long intervals, i.e., two or three times the median interval, when the EGM is not stored.

As illustrated in FIG. 10, if one of the undersensing criteria are not met, No in Block 950, the signal is determined to be spontaneous and regular, Yes in Block 302 of FIG. 3, and the process continues with the determination of the A/V ratio, Block 304 of FIG. 3 as described above. If one of the undersensing criteria are met, Yes in Block 950 and if the undersensing is repairable, the location of the undersensed event is determined, Block 952. The undersensing is repairable if the median AA interval is between 300 and 750 ms (inclusive), and if the interval containing the undersensed event is a multiple of 2 or 3 times the median AA interval. If undersensing is not repairable, such as in the cases where the atrial sensed interval is >2500 or there are only 9 atrial events prior to detection, then undersensing is reported but not repaired.

According to an embodiment of the present invention, if the interval 967 is two times the median AA interval, the location of the undersensed event is determined by inserting a single sensed atrial event at the midpoint of the interval 967. If the interval 965 is three times the median AA interval, the location of the undersensed event is determined by inserting a first sensed atrial event at a distance corresponding to the median AA interval from a starting point 973 of the interval, and a second interval at a distance corresponding to the median AA interval prior to an end point 975 of the interval 965.

Some of the techniques described above may be embodied as a computer-readable medium comprising instructions for a programmable processor such as microprocessor 142, pacer/device timing circuit 178 or control circuit 144 shown in FIG. 3. The programmable processor may include one or more individual processors, which may act independently or in concert. A "computer-readable medium" includes but is not limited to any type of computer memory such as floppy disks, conventional hard disks, CR-ROMS, Flash ROMS, nonvolatile ROMS, RAM and a magnetic or optical storage medium. The medium may include instructions for causing a processor to perform any of the features described above for initiating a session of the escape rate variation according to the present invention.

While a particular embodiment of the present invention has been shown and described, modifications may be made. It is therefore intended in the appended claims to cover all such changes and modifications, which fall within the true spirit and scope of the invention.

The invention claimed is:

1. A method of post-processing of sensing data generated by and stored within an implantable medical device, comprising:

receiving the sensing data from the implantable medical device with an external access device, wherein the sensing data includes sensed atrial events and sensed ventricular events;

determining, with the external access device, in response to the received data, instances where the implantable medical device identified a cardiac event being detected in response to the sensing data; and determining, with the external access device, in response to the received sensing data, which one of the atria or the ventricles of a heart associated with the sensing data initiated conduction of the heart by at least determining which one of the sensed ventricular events or the sensed atrial events initiated conduction of the heart, wherein determining which one of the sensed ventricular events or the sensed atrial events initiated conduction of the heart comprises:

identifying a spatial reference point within a portion of the received sensing data comprising sensed atrial and ventricular events from a plurality of cardiac cycles, wherein the spatial reference point is an identified cardiac interval within the received sensing data;

generating a window around the spatial reference point, the window comprising a subset of the sensed ventricular events, in response to the spatial reference point, wherein the subset of the sensed ventricular events comprises a plurality of the sensed ventricular events;

determining numbers of the sensed atrial events between the ventricular events within the subset of sensed ventricular events; and determining which one of the sensed ventricular events or the sensed atrial events initiated conduction of the heart based on the numbers of the sensed atrial events between the ventricular events within the subset of sensed ventricular events.

2. The method of claim 1, wherein identifying a spatial reference point comprises determining, starting with a last ventricular sense event associated with a cardiac event being detected, when a predetermined number of sequential adjacent intervals occurring prior to the last ventricular sense event are greater than an onset threshold.

3. The method of claim 2, further comprising:
  determining a first median of first sensing data of the plurality of received sensing data occurring just prior to the cardiac event being detected;
  determining a second median of second sensing data of the plurality of received sensing data occurring prior to a number of intervals to detection associated with the cardiac event being detected; and
  determining a difference between the first median and the second median, wherein an abrupt onset is determined in response to the difference being greater than a predetermined threshold, wherein the onset threshold is set as a sum of the first median and a portion of the determined difference.

4. The method of claim 1, wherein determining numbers of the sensed atrial events between the ventricular events within the subset of sensed ventricular events and determining which one of the sensed ventricular events of the sensed atrial events initiated conduction of the heart based on the numbers or the sensed atrial events between the ventricular events within the subset of sensed ventricular events comprises:
  determining a number of sensed atrial events between each of a plurality of adjacent pairs of the sensed ventricular events within the subset of sensed ventricular events within the window,
  wherein the sensed atrial events are determined to be initiating the conduction in response to no sensed atrial events occurring between more than one of the adjacent pairs and only one sensed atrial event occurring between each of the other of the adjacent pairs of the sensed ventricular events within the window, and the sensed ventricular events are determined to be initiating conduction in response to no sensed atrial events occurring between only one of the adjacent pairs and only one sensed atrial event occurring between each of the other of the adjacent pairs of the sensed ventricular events within the window.

5. A system for post-processing of sensing data associated with identification of a cardiac event, comprising:
  an implantable medical device generating and storing a plurality of sensing data, wherein the sensing data includes sensed atrial events and sensed ventricular events;
  an access device located externally from the implantable medical device; and
  an interface for receiving the sensing data from the implantable medical device with the external access device,
  wherein the external access device determines, in response to the received data, instances where the medical device identified a cardiac event being detected in response to the sensing data, and which one of the atria or the ventricles of a heart associated with the sensing data initiated conduction of the heart by at least determining which one of the sensed ventricular events and the sensed atrial events is initiating conduction of the heart, wherein the access device:
    identifies a spatial reference point within a portion of the received sensing data comprising sensed atrial and ventricular events from a plurality of cardiac cycles;
    generates a window around the spatial reference point, the window comprising a subset of the sensed ventricular events, in response to the spatial reference point, wherein the subset of the sensed ventricular events comprises a plurality of the sensed ventricular events, and wherein the spatial reference point is an identified cardiac interval within the received sensing data;
    determines numbers of the sensed atrial events between the ventricular events within the subset of sensed ventricular events; and
    determines which one of the sensed ventricular events or the sensed atrial events initiated conduction of the heart based on the numbers of the sensed atrial events between the ventricular events within the subset of sensed ventricular events.

6. The system of claim 5, wherein the external access device identifies a spatial reference point by determining, starting with a last ventricular sense event associated with a cardiac event being detected, when a predetermined number of sequential adjacent intervals occurring prior to the last ventricular sense event are greater than an onset threshold.

7. The system of claim 6, wherein the external access device determines a first median of first sensing data of the plurality of received sensing data occurring just prior to the cardiac event being detected, a second median of second sensing data of the plurality of received sensing data occurring prior to a number of intervals to detection associated with the cardiac event being detected, and a difference between the first median and the second median, wherein an abrupt onset is determined in response to the difference being greater than a predetermined threshold, and wherein the onset threshold is set as a sum of the first median and a portion of the determined difference.

8. The system of claim 5, wherein, to determine numbers of the sensed atrial events between the ventricular events within the subset of sensed ventricular events and determine which one of the sensed ventricular events or the sensed atrial events initiated conduction of the heart based on the numbers of the sensed atrial events between the ventricular events within the subset of sensed ventricular events, the external access device:
  determines a number of sensed atrial events between each of a plurality of adjacent pairs of the sensed ventricular events within the subset of sensed ventricular events within the window,
  wherein the sensed atrial events are determined to be initiating the conduction in response to no sensed atrial events occurring between more than one of the adjacent pairs and only one sensed atrial event occurring between each of the other of the adjacent pairs of the sensed ventricular events within the window, and the sensed ventricular events are determined to be initiating conduction in response to no sensed atrial events occurring between only one of the adjacent pairs and only one sensed atrial event occurring between each of the other of the adjacent pairs of the sensed ventricular events within the window.

* * * * *